(12) United States Patent
Foord et al.

(10) Patent No.: US 10,325,754 B2
(45) Date of Patent: Jun. 18, 2019

(54) ION IMPLANTATION TO ALTER ETCH RATE

(71) Applicant: FEI Company, Hillsboro, OR (US)

(72) Inventors: David Foord, Portland, OR (US); Chad Rue, Portland, OR (US)

(73) Assignee: FEI COMPANY, Hillsboro, OR (US)

( * ) Notice: Subject to any disclaimer, the term of this patent is extended or adjusted under 35 U.S.C. 154(b) by 56 days.

(21) Appl. No.: 14/759,158

(22) PCT Filed: Jan. 10, 2014

(86) PCT No.: PCT/US2014/011057
§ 371 (c)(1),
(2) Date: Jul. 2, 2015

(87) PCT Pub. No.: WO2014/110379
PCT Pub. Date: Jul. 17, 2014

(65) Prior Publication Data
US 2015/0348752 A1    Dec. 3, 2015

Related U.S. Application Data

(60) Provisional application No. 61/751,360, filed on Jan. 11, 2013.

(51) Int. Cl.
*B01D 59/44* (2006.01)
*H01J 37/305* (2006.01)
(Continued)

(52) U.S. Cl.
CPC ............ *H01J 37/3056* (2013.01); *G01N 1/32* (2013.01); *H01J 37/3171* (2013.01);
(Continued)

(58) Field of Classification Search
CPC ............................................ H01J 2237/31745
See application file for complete search history.

(56) References Cited

U.S. PATENT DOCUMENTS

| 4,971,896 A | 11/1990 | Kawabe et al. |
| 8,277,672 B2 | 10/2012 | Makarov |

(Continued)

FOREIGN PATENT DOCUMENTS

| CN | 1622281 A | 6/2005 |
| CN | 102564818 A | 7/2012 |

(Continued)

OTHER PUBLICATIONS

Mayer, Joachim, et al. "TEM sample preparation and FIB-induced damage." MRS bulletin 32.05 (2007): 400-407.*
(Continued)

*Primary Examiner* — Jason Berman
(74) *Attorney, Agent, or Firm* — Denton W. McAlister

(57) ABSTRACT

Implanting a material in a pattern hardens the material in the pattern for subsequent etching. When the region is etched, by ion beam sputtering, chemically enhanced charged particle beam etching, or chemical etching, a thicker structure remains because of the reduced etch rate of the hardened pattern. The invention is particularly useful for the preparation of thin lamella for viewing on a transmission electron microscope.

14 Claims, 6 Drawing Sheets

(51) Int. Cl.
*H01J 37/317* (2006.01)
*G01N 1/32* (2006.01)

(52) U.S. Cl.
CPC ............... *H01J 2237/31713* (2013.01); *H01J 2237/31745* (2013.01); *H01J 2237/31749* (2013.01); *Y10T 428/24479* (2015.01)

(56) References Cited

U.S. PATENT DOCUMENTS

| | | | |
|---|---|---|---|
| 2002/0019137 | A1 | 2/2002 | Tsung et al. |
| 2004/0148771 | A1 | 8/2004 | Ma et al. |
| 2009/0309018 | A1 | 12/2009 | Smith et al. |
| 2012/0056088 | A1 | 3/2012 | Rue |

FOREIGN PATENT DOCUMENTS

| | | | |
|---|---|---|---|
| CN | 102809496 | A | 12/2012 |
| EP | 0061350 | A1 | 9/1982 |
| EP | 2413126 | A2 | 2/2012 |
| EP | 2530700 | A2 | 12/2012 |
| JP | S57157523 | A | 9/1982 |
| JP | H03-071632 | | 3/1991 |
| JP | H07151658 | A | 6/1995 |
| JP | 2000230891 | A | 8/2000 |
| JP | 2005055387 | A | 3/2005 |
| JP | 2009198412 | A | 9/2009 |
| JP | 2009544120 | A | 12/2009 |
| JP | 2012042461 | A | 3/2012 |

OTHER PUBLICATIONS

Pälvi Sievilä, Nikolai Chekurov, and Ilkka Tittonen. 2010. The fabrication of silicon nanostructures by focused-ion-beam implantation and TMAH wet etching. Nanotechnology, vol. 21, No. 14, 145301, 6 pages.*
Lechner, L., et al., "Improved Focused Ion Beam Target Preparation of (S)TEM Specimen—A Method for Obtaining Ultrathin Lamellae," Microscopy and Microanalysis, (2012), pp. 379-384, vol. 18.
E. Holmstrom et al., "Atomic-scale effects behind structural instabilities in Si lamellae during ion beam thinning," AIP Advances, American Institute of Physics, Mar. 1, 2012, vol. 2, No. 1, 13 pgs.
K. Nishioka et al., "Reactive Ion Beam Etching Using a Selective Gallium Doping Methods," Japanese Journal of Applied Physics, Sep. 9, 1989, vol. 28, No. 9, pp. 1671-1672.
S. K. Ray et al., "Chemically Assisted Ion Beam Etching of Silicon and Silicon Dioxide Using SF6," Plasma Chemistry and Plasma Processing, Dec. 1995, vol. 15, No. 4, 10 pgs., New York, NY.
Chekurov, N. et al., "The fabrication of silicon nanostructures by local gallium implantation and cryogenic deep reactive ion etching," Nanotechnology, Jan. 14, 2009, vol. 20, No. 6, 065307, 5 pages.
Schmidt, B. et al., Etch Rate Retardation of Ga+ -Ion Beam-irradiated Silicon; J. Electrochem Soc. 2005, vol. 152, Issue 11, pgs. G875-G879.
Unknown, "Fabrication of Nanostructure Array by Ion-Bombardment-Retarded Etching," Molecular Nano-Engineering Lab., TANII Research Group, Waseda Univ., obtain from the Internet Jan. 27, 2018, http://www.tanii.nano.waseda.ac.jp/ibre.html.

* cited by examiner

ION IMPLANTATION TO ALTER ETCH RATE

TECHNICAL FIELD OF THE INVENTION

The present invention relates to the preparation of samples for transmission electron microscopy (TEM) and scanning transmission electron microscopy (STEM).

BACKGROUND OF THE INVENTION

A transmission electron microscope (TEM) enables observers to form images of extremely small features, on the order of nanometers to fractions of Angstroms. TEM images allow analysis of the internal structure of a sample. In a TEM, a broad beam of electrons impacts the sample, and electrons that are transmitted through the sample are focused to form an image of the sample. The sample must be sufficiently thin to allow many of the electrons in the primary beam to travel though the sample and exit on the opposite site.

A thin TEM sample cut from a bulk sample material is known as a "lamella." Lamellae are typically less than 100 nanometers (nm) thick, but for some applications a lamella must be considerably thinner. In the semiconductor industry, TEM and STEM analysis is becoming especially important to characterize the smallest and most critical structures. Lamella preparation is a critical step in TEM analysis. The continuing demand to reduce the size of transistors results in the need to further decrease the thickness of lamellae to provide samples that contain one discrete transistor structure only. The minimum feature size or "pitch" used in semiconductor manufacturing is moving toward 22 nm, so it will be desirable to produce lamella having a thickness of around 10 nm. Lamellae having thicknesses of less than 20 nm are challenging to produce in a reliable and repeatable manner.

Such thin lamellae are subject to mechanical failure due to the lack of structural integrity—warping, bending, and erosion of critical areas often occurs in very thin samples. Since the required thickness of lamellae is decreasing, there is a need for a method of providing and maintaining structural integrity of thin samples.

Methods for TEM lamella preparation typically use a focused ion beam (FIB) system. The accuracy of lamella thickness and the final lamella center location were based on the accuracy of the placement of FIB milling operations. In an automated work flow, milling is typically performed with respect to some feature or fiducial on the top surface of the substrate from which the TEM sample lamella is to be milled.

As lamellae less than 20 nm thick are desired, the required increased level of precision requires a higher operator skill. Further, the success rate of lamella samples decreases dramatically as the thickness decreases, for example, to less than 10 nm.

Prior art lamella reinforcing techniques, such as the method taught by Lechner in EP 2413126, involve shaping the lamella to leave certain areas thicker than others for structural support. Such methods leave "windows" of thinner regions surrounded by thicker regions, but such windows can limit the field of view which in turn affects the amount of information that can be obtained from the lamella. Windowing also adds complexity and process time. Further, a high level of operator skill is required to direct the focused ion beam to different regions to leave varying levels of thickness within the lamella. Thus, what is needed is an improved method and apparatus to reinforce lamella samples.

SUMMARY OF THE INVENTION

An object of the invention is to produce a microscopic pattern on a sample by implanting ions into the sample and then processing the sample, with the implanted regions behaving differently from the unimplanted regions under the processing.

In some embodiments, ions are implanted into regions of the sample using a focused ion beam, and the sample is processed, such as by etching, with material in the implanted regions being removed more slowly than the non-implanted regions, leaving a raised pattern corresponding to the implanted regions, or material being removed more rapidly, leaving a depressed region corresponding to the implanted regions.

In accordance with some embodiments of the invention, a hardening material is implanted into regions of the lamella to strengthen the lamella. In some embodiments, the implanted material makes the lamella resistant to ion beam processing, leaving the implanted area thicker than other regions of the lamella, thereby forming a reinforcing structure that provide additional support to the lamella.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

Figure 1:
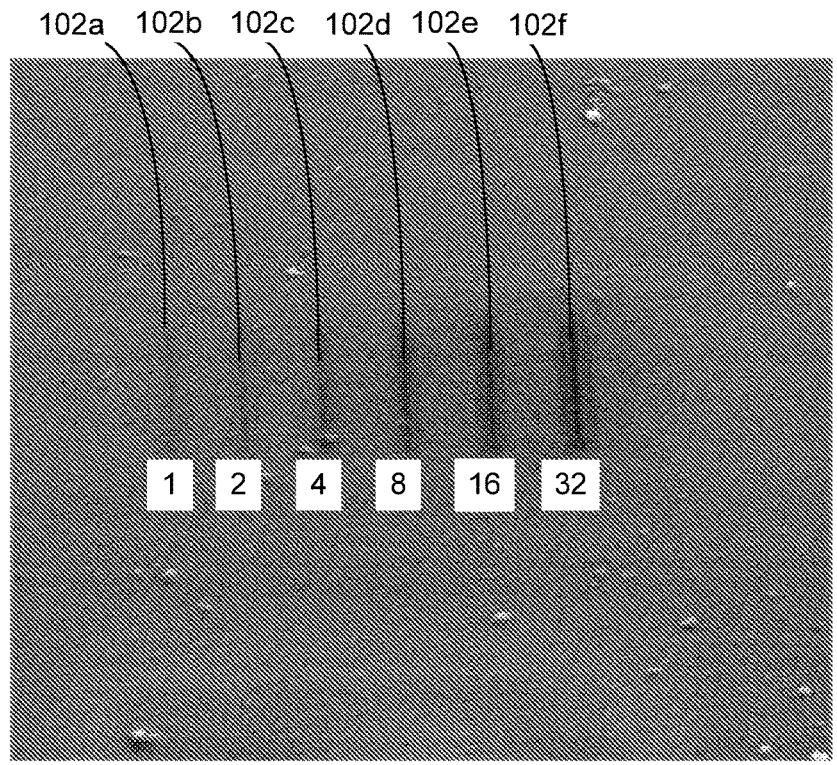
FIG. 1 is a photomicrograph showing beryllium (Be) implantation in lines in a silicon work piece, with the duration of the implantation varying from 1 second to 32 seconds.

In accordance with some embodiments of the invention, a material is provided to harden a region of a work piece before etching. The region with the added material etches at a slower rate than the surrounding region without the added material, leaving structures defined by the added material. The material can be added, for example, by ion implantation, which allows for the precise definition of structures having dimensions in the nanometer range. In some embodiments, the implanted areas etch at faster rate, leaving depressions instead of raised regions.

Etching of the material after implantation of the ions, can be performed, for example, using focused ion beam etching, broad beam (spot size greater than 0.5 µm) ion etching, beam-induced chemical etching, chemical etching without a beam, or laser beam etching. Beam-induced etching can be induced, for example, using an ion beam, an electron beam, a cluster beam, a neutral beam, a laser beam, or an optical beam. Because the area etched is typically larger than the implanted area, the etching is preferably performed, if a beam is used, using a beam with a larger spot size than the beam that implants the ions.

Applicants have found, for example, that beryllium (Be) ions harden various work piece materials, including silicon (Si), silicon dioxide ($SiO_2$), and copper (Cu), making the work piece more resistive to etching by ion sputtering. The ions are typically implanted in a first region, and then a second region, preferably a superset of the first region, is etched, for example, such as by being processed using a second beam, such as an ion beam, an electron beam, or a laser beam, or other process, such as chemical etching.

Embodiments of the invention are particularly useful for forming lamellae for TEM imaging and analysis. The method can be used to form reinforcing structures in lamellae, which strengthen each lamella to prevent bending and erosion. Use of the invention makes the process of lamellae creation more reproducible, increasing the success rate. While the desired width of the reinforcing structures will vary with the specific application, the minimum width of the strengthened region is limited only by the resolution of the spot size of the implanting beam, or other material placement method. In some embodiments, a single focusing column is used to produce the beam of the implanted ions and the beam of the milling ions. For example, a liquid metal alloy source, such as the one described in U.S. Pat. No. 4,775,818, to Clark Jr., et al., for "Liquid Metal Ion Source and Alloy," or a plasma ion source such as the one described in U.S. Pat. Pub. 2009/0309018 of Smith et al. for a "Multi-Source Plasma Focused Ion Beam System," can be used with a mass filter to select the ions, readily switching between a beam of the strengthening ions and a beam of the milling ions. Typically, different ion species are used for implanting and etching. The same species could be used preferably at different beam energies. Other embodiments can use a different ion column system to produce the different beams. Embodiments of the invention can eliminate the need for beam-induced deposition of reinforcing structure. Sacrificial protective caps, typically of platinum or tungsten, are used in lamella preparation. Embodiments of the invention can also be used to reinforce sacrificial protection caps, reducing erosion of the cap.

In certain embodiments, the Be hardening allows lamellae less than 20 nm in thickness and even more preferably less than 10 nm in thickness, to retain their structural integrity and be capable of being inspected in TEM or STEM modes. Prior art thinning methods that do not provide strengthening are not capable of producing sections less than 10 nm as these sections exhibit stress relaxation and a variety of destructive failure mechanisms such as curling, bending, or splitting.

FIG. 1 is a photomicrograph showing "burns" or lines 102a-102f on the surface of a work piece after Be was implanted for 1 second, 2 seconds, 4 seconds, 8 seconds, 16 seconds and 32 seconds, respectively.

Figure 2:
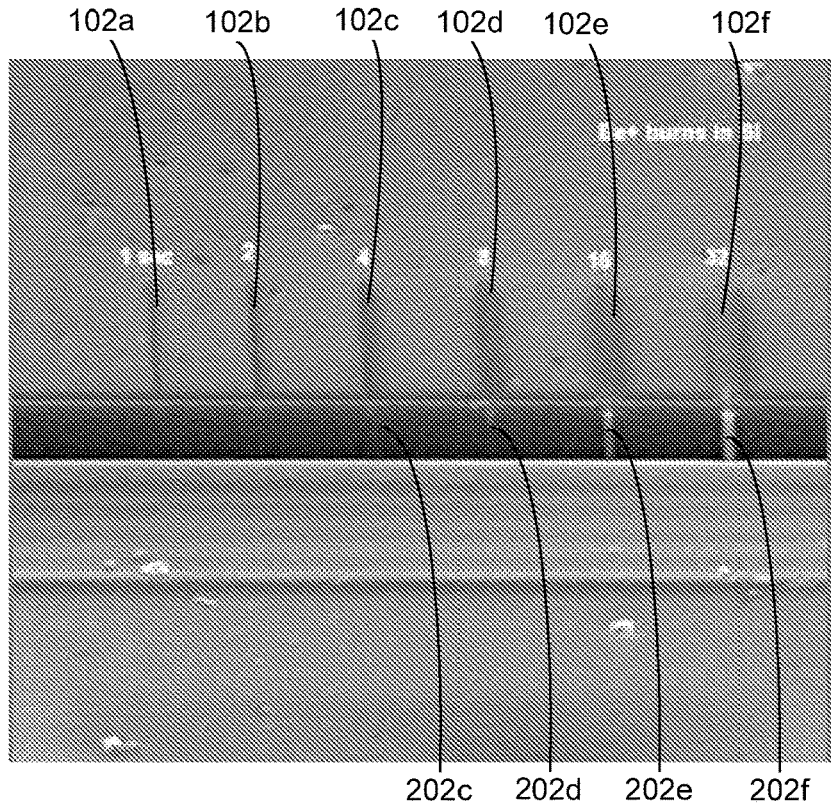
FIG. 2 is a photomicrograph showing a cross section of the lines of FIG. 1.

FIG. 2 shows a cross section milled though the region of FIG. 1 using a focused ion beam. The ion beam was directed normal to the surface and normal to the Be implant lines. The structures 202c-202f in the cross section below the implanted region show that the ion beam milled the implanted region more slowly than the surrounding region, leaving a "shadow" beneath the implanted region. That is, the implanted region shielded the underlying region. The resistance to milling varies with the amount of Be implanted, which depends on the time that that the Be beam is directed to the work piece. From FIG. 2, structure 202f, which lies under the line 102f onto which the Be was implanted for 32 seconds, is more pronounced than structure 202e, which lies under the line 102e onto which the Be was implanted for 16 seconds. There is no visible structure under lines 102a and 102b, which were radiated for 1 second and 2 seconds, respectively.

Figure 3:
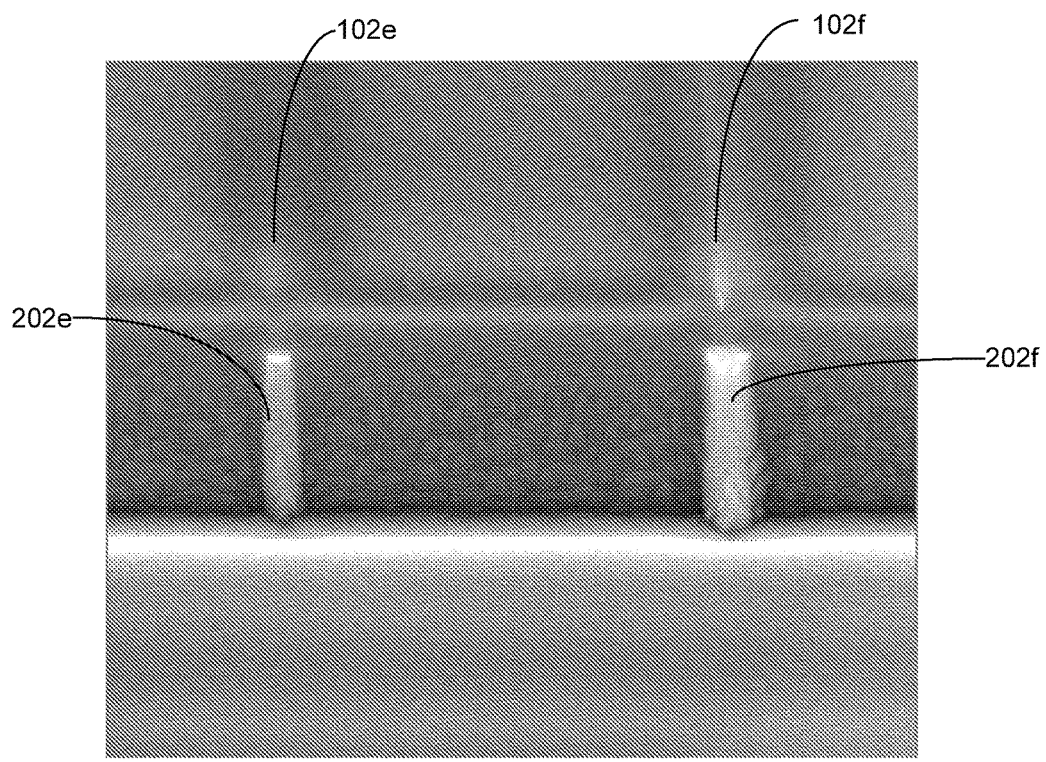
FIG. 3 is a photomicrograph showing a portion of the cross section of FIG. 2 at higher magnification.
Figure 4:
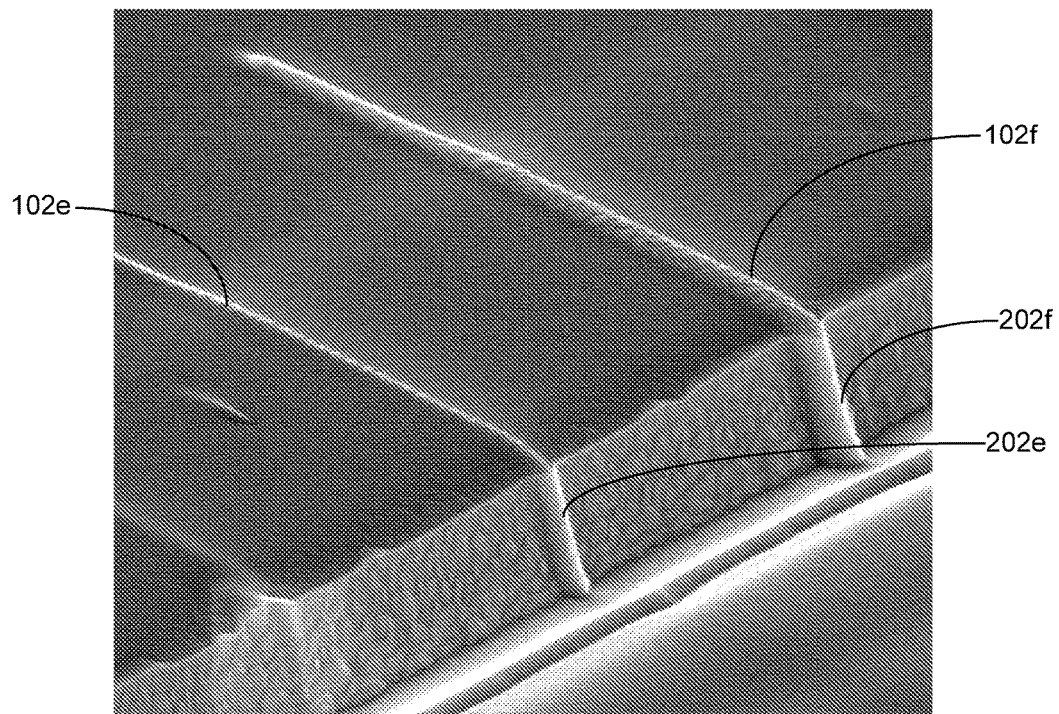
FIGS. 4 and 5 are photomicrographs images of the cross section of FIG. 2.
Figure 5:
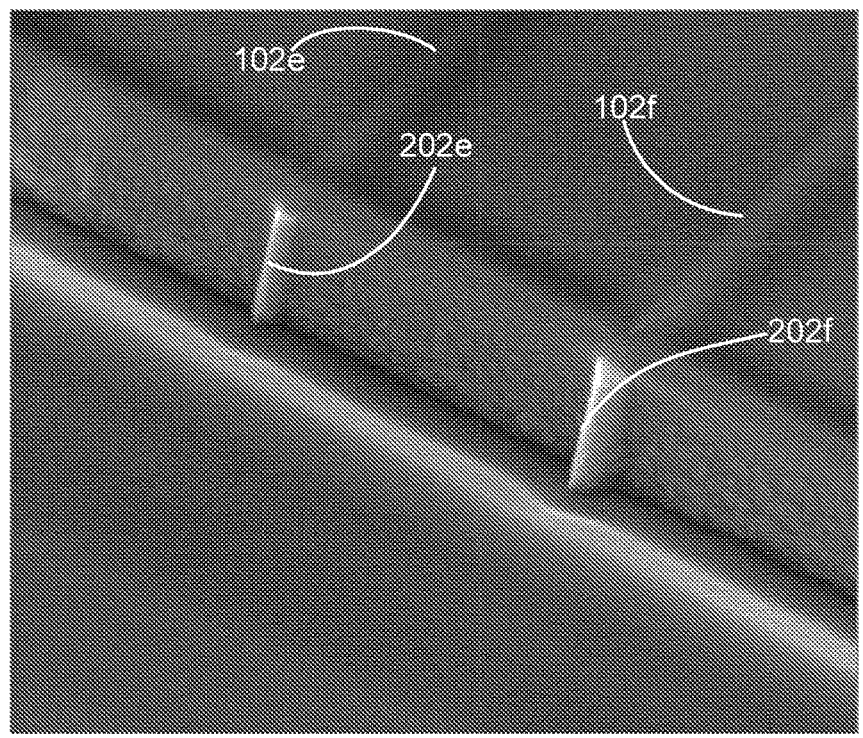

FIG. 3 is a photomicrograph showing structures 202e and 202f at greater magnification. FIGS. 4 and 5 are photomicrographs showing additional views of the milled cross section.

Figure 6:
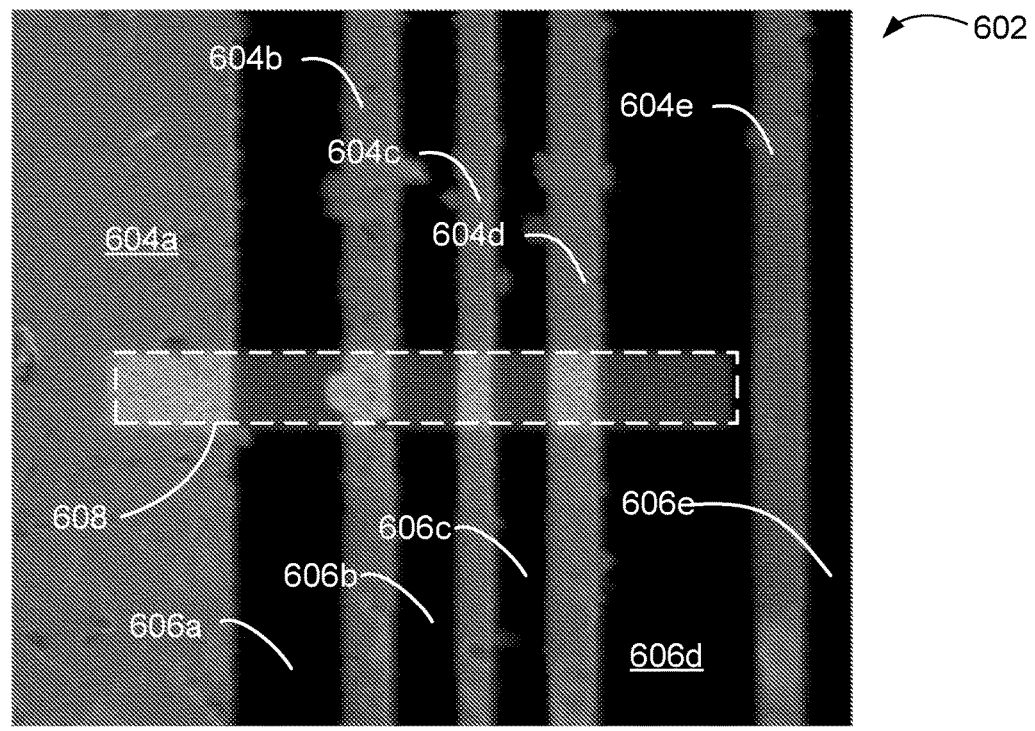
FIG. 6 is a photomicrograph showing a substrate of different materials and showing a region to be implanted with Be ions.

FIG. 6 shows a non-homogenous surface 602 that includes regions 604a, 604b, 604c, 604d, and 604e of copper, which appear grey in the charged particle beam image, separated by regions of silicon dioxide 606a, 606b, 606c, and 606d, to 606e, which appear black in the charged particle beam image. FIG. 6 also shows a region 608 of the surface 602 that is to be implanted with Be. Note that the region 608 to be implanted extends only part way through copper region 604a and silicon dioxide region 606d, and does not extend into copper region 604e or silicon dioxide region 606e.

Figure 7:
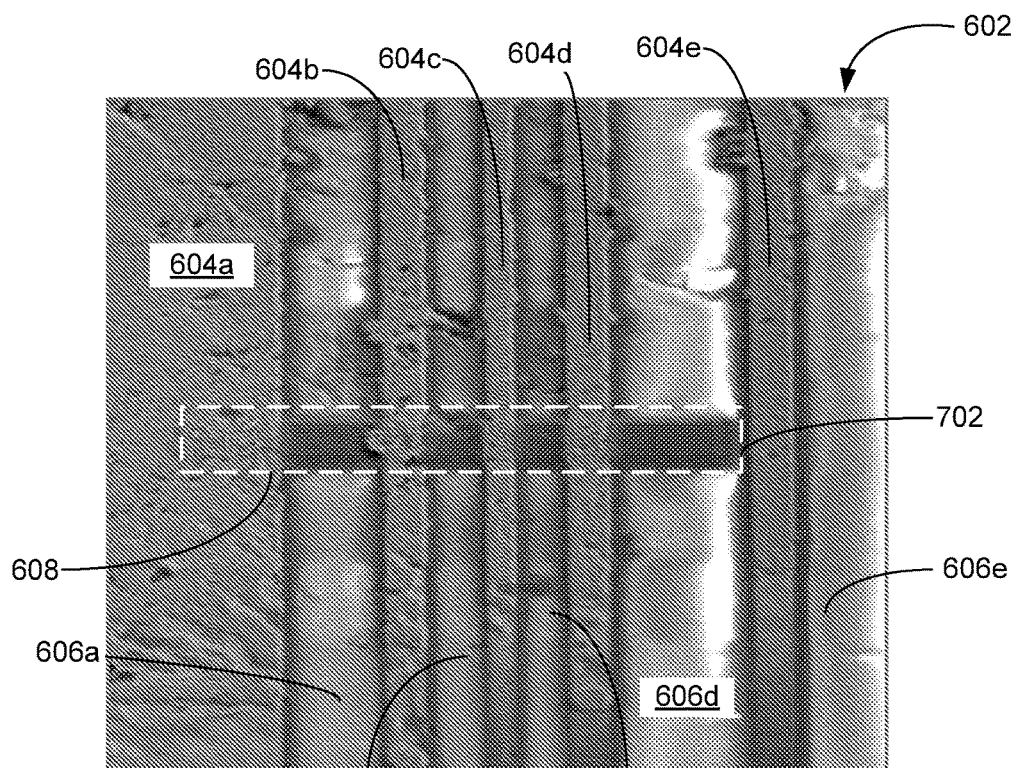
FIG. 7 is a photomicrograph showing the substrate of FIG. 6 with implanted Be ions.
Figure 8:
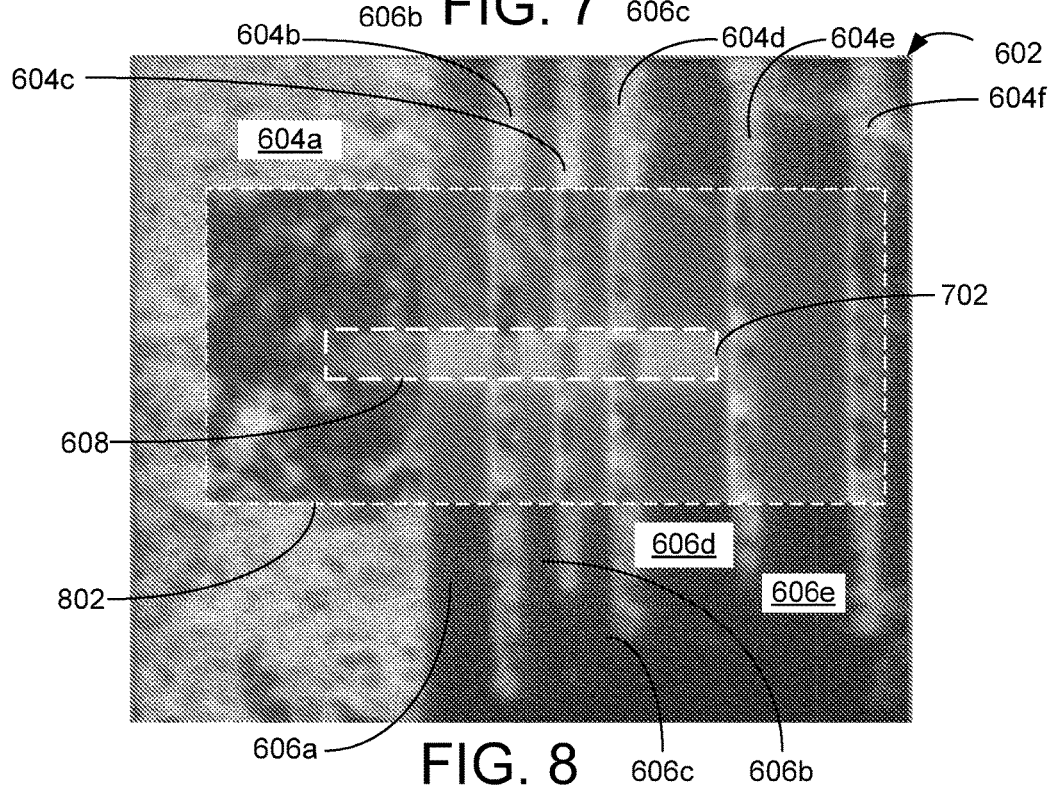
FIG. 8 is a photomicrograph showing the substrate of FIG. 7 showing the region to be milled.
Figure 9:
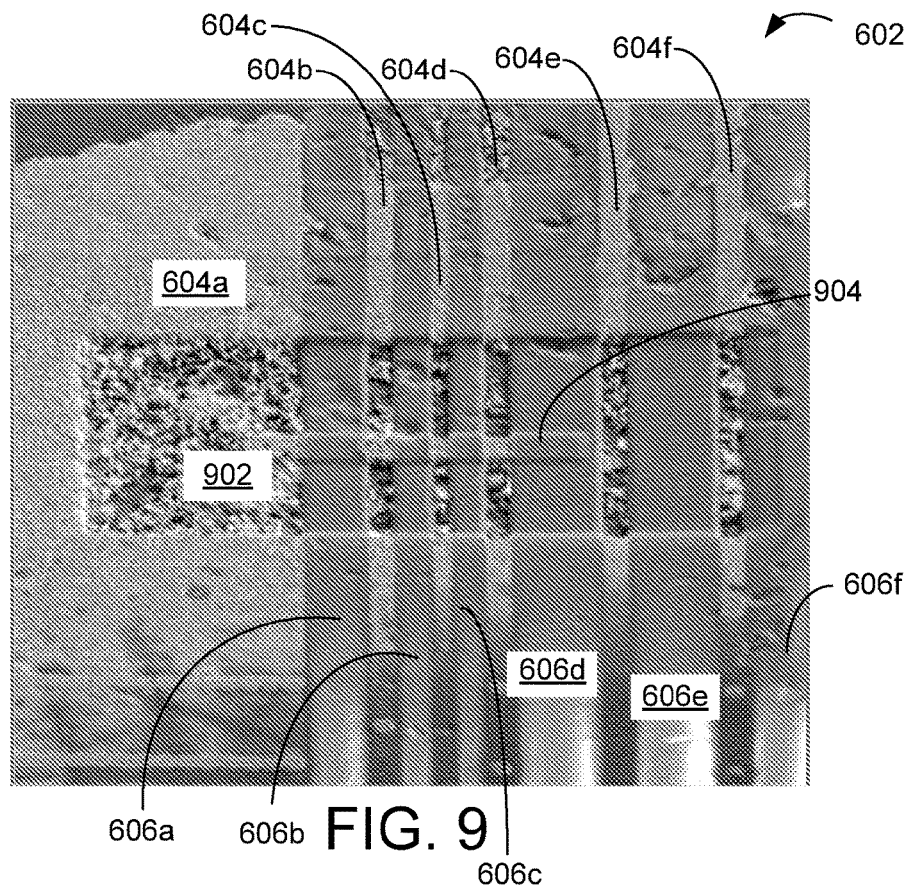
FIG. 9 is a photomicrograph showing the substrate of FIG. 7 after milling by gold ions.

FIG. 7 shows the hardened region 702 after implantation of Be. The images in FIGS. 6 and 7 were obtained using different system settings, so the substrate appears different in the two images. FIG. 8 shows a region 802 to be milled using gold ions. Preferably, the gold ions are obtained from the same liquid metal ion alloy source as the Be ions. A mass filter can be used to selectively deliver either Be ion or gold ions to the work piece, with the column optics being adjusted to focus the selected ions at the work piece. FIG. 9 shows the results of the milling a region 902, corresponding to region 802 of FIG. 8, using a beam of gold ions.

FIG. 9 shows that surface material is etched away in the milled region 902, but the portion of region 902 that had implanted Be is not milled as deeply as the rest of the region, leaving a raised strip 904 where the Be was implanted. Note that copper region 604a shows that the raised strip 904 partly crosses the copper region and silicon dioxide region 606d also shows that the raised strip extends only partly across region 606d, the raised area corresponding to the portion into which beryllium was implanted. In copper regions 604e and 604f, and in silicon dioxide regions 606e and 606f, there was no beryllium implanted, and there are no raised regions.

FIGS. 6-9 show that Be reduces the milling rate on copper and silicon dioxide, as well as on silicon, as shown by FIGS. 1-5.

Figure 10:
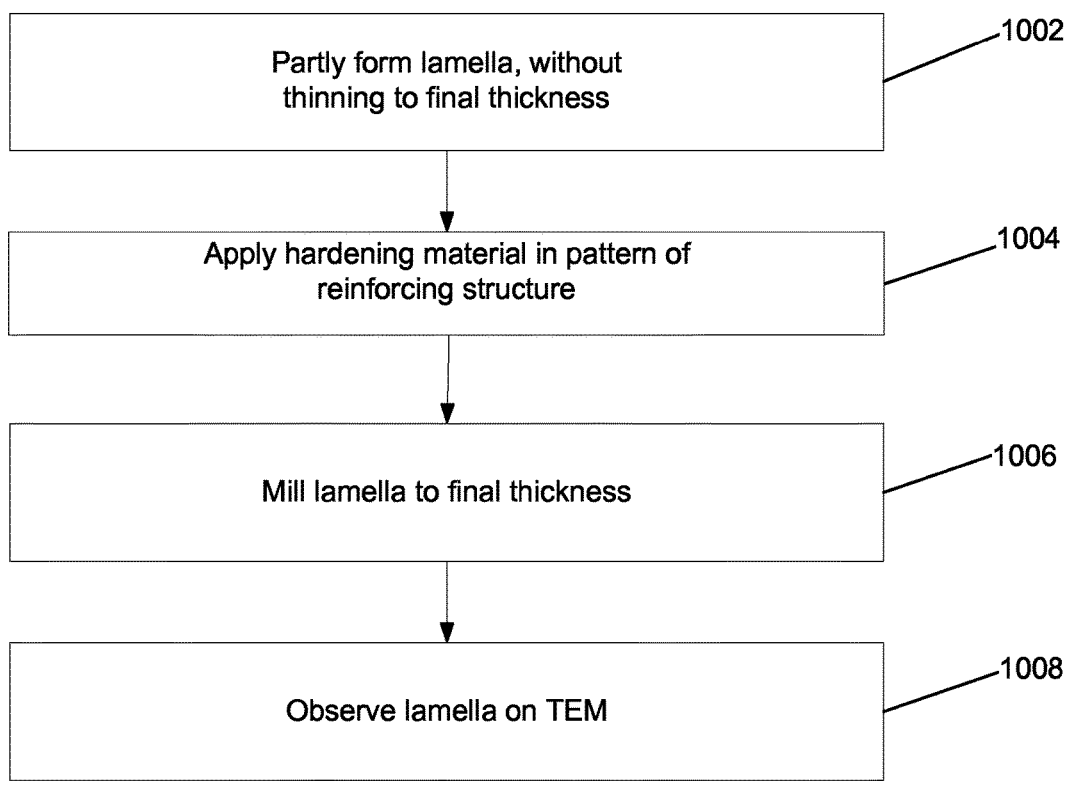
FIG. 10 is a flowchart showing the steps of an embodiment of the invention used in forming a lamella.

FIG. 10 is a flow chart showing steps of forming a lamella in accordance with an embodiment of the invention. In step 1002, a lamella is partly formed. Any lamella preparation procedure, such the one described in WO2012/103534 for "TEM Sample Preparation," which is hereby incorporated by reference, can be used. The lamella is preferably thinned, but not thinned all the way to its final thickness in step 1002.

Figure 11:
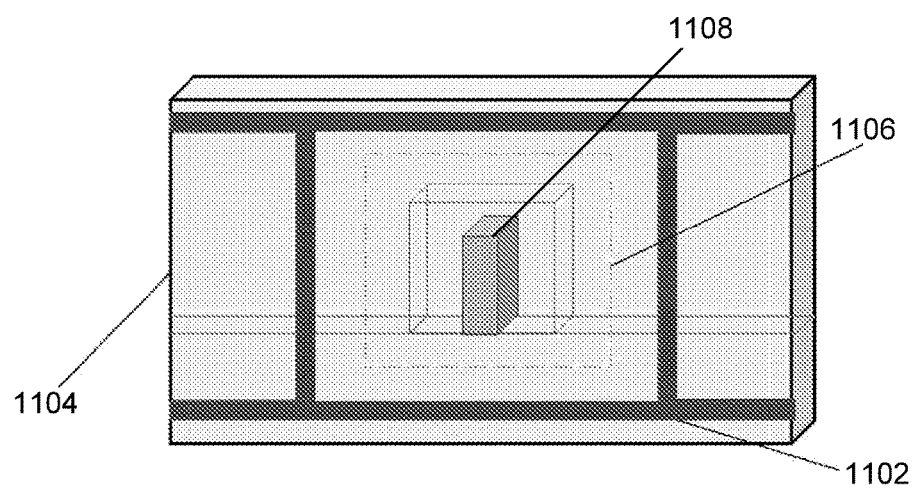
FIG. 11 shows a layout of a lamella, showing a region of interest and a design for a reinforcement structure to be created in accordance with an embodiment of the invention.

FIG. 11 is a diagram showing an arrangement of a hardened area 1102 structurally reinforcing the lamella 1104 without affecting a region of interest 1106 defined around a feature 1108.

In step 1004, the hardening material is applied to the lamella in a pattern corresponding to the desired reinforcing structure. In one embodiment, the hardening material is Be and it is applied using a focused beam of Be ions, from a liquid metal alloy ion source at a beam energy of 30 keV and a beryllium dose of a few tenths of $nC/\mu m^2$. In step 1006, the lamella is milled with a focused ion beam to its final thickness. The structure will be formed by the mill resistance of the hardened regions 1102, which produces a reinforcement structure. In step 1008, the lamella is viewed on a transmission electron microscope.

The hardening process is not limited to beryllium ions and other ions can be used to provide a similar effect. For example, $Li^+$, $Mg^+$, and $Ca^+$ may be useful to implant into Si or other materials. Other material that may be useful for implanting to harden a material include $Ga^+$, $Xe^+$, $Ar^+$, $O^+$, $In^+$, $Si^+$, $Kr^+$, and $Bi^+$. Implanting may be useful to harden almost any material, but the process may be particularly useful in applications that harden silicon, silicon nitride, silicon carbide, tungsten, SiGe, low-k dielectric materials ("carbon-doped oxide"), tantalum, tantalum nitride, titanium, titanium nitride, aluminum.

A preferred hardening material, when applied, preferably produces an etch rate at least 10% less, more preferably 20% less, and most preferably 30% less than the etch rate of the work piece material without the implant. The material preferably has no affect on the region of interest. A preferred hardening material is one that can be readily obtained from an ion source, such as a liquid metal alloy source or a plasma source, and readily focused into a beam having a spot size of less than 10 nm. The preferred material does not readily diffuse in the material into which it is being applied to avoid affecting the region of interest.

For ion implantation, the ion type, energy, and dose should all be selected to minimize mechanical sputtering as much as possible. For example, light ions can be safely used at high energies (30 keV) and moderate dose (0.1-0.5 $nC/\mu m^2$), whereas heavier ions would result in significant sputtering at these energies. To determine a suitable dose for a specific ion/material/energy combination, a useful approach is to first perform a survey experiment in a non-critical area. For example, one can irradiate regions with a range of doses from 0.1-1.0 $nC/\mu m^2$ at the desired energy, and observe the effect of those various exposures with high-resolution SEM imaging or AFM analysis. Regions which show significant milling or surface swelling are over-exposed, and such conditions are not preferred for hardening purposes. The preferred dose is the highest dose possible whilst maintaining minimal mechanical damage. For light ions, the sputter rate may increase as the energy is lowered, so the user must exercise care to avoid entering a region in which mechanical sputtering becomes significant. Additionally, lower ion energies also have lower spatial resolution (larger spot size), which makes it more difficult for the user to pattern a precise hardening structure on small samples such as TEM lamellae. In general, the preferred conditions for effective material hardening are high energy, light ion mass, and doses tuned to just below the threshold for visible mechanical damage. The hardening process has been demonstrated to work equally well on crystalline (Si), polycrystalline (Cu) and amorphous materials ($SiO_2$).

Based on the examples, and guidance provided above, a skilled person can readily select an ion species, beam energy and dose to harden a substrate for a particular application.

In some embodiments, the present invention allows more localized strengthening of a lamella and is faster and less complex than the prior art "window" methods.

In some embodiments of the present invention, implanted Be ions provide support regions around a region of interest. As the thinning process continues, the implanted ion regions have a slower rate of material removal as compared to regions without implanted $Be^+$ ions, resulting in thicker support structures around the region of interest without the need for additional depositions.

Embodiments of the invention can be used to create a pattern or region that is resistant to ion beam sputtering, as well as a pattern or region that is resistant to charged particle beam-induced chemical etching, in which the beam provides the activation energy for a chemical reaction with a precursor material, typically a gas. In such embodiments, a first beam is directed toward the sample to implant atoms into the sample to create a patterned area that is intended to resist subsequent removal by the ion beam. A second beam is directed toward the sample in the presence of a precursor gas. Energy from the second beam decomposes the adsorbed precursor molecules, resulting in a chemical reaction between the substrate material and the precursor gas to etch the substrate. The second beam may be an ion beam of the same or a different species, an electron beam, a neutral beam, or a laser beam. The region of implanted atoms reduces the etch rate to leave a reinforcing structure.

In some embodiments, the implanted regions are resistant not only to beam induced etching, but also to spontaneous etching. For example, the inventors have noted that regions of Si implanted with Au ions show resistance to chemical etching by $XeF_2$. Note that the etching chemistry may or may not require energy from a second beam. In the case of $XeF_2$ on Si, there are both beam-driven and spontaneous etching components to the material removal. The Au implantation appears to reduce the etch rate of the Si in either case (with or without energy from a second ion beam during the etch step). Implantation can reduce the etching rate for both a beam-driven etch step or a non beam-driven (chemistry only) etch step.

In some embodiments of the invention, a beam of ions is directed toward a region of the surface. A larger region of the surface, a superset of the implanted region, is then exposed to a chemical for etching, with the implanted areas etching more slowly to produce a raised pattern on the surface.

In other embodiments, the implanted regions may have the opposite effect—that is, milling rates are increased in selected areas due to ion exposure. In such embodiments, a beam of ions is directed to a surface to implant ions into a region or pattern, and then the surface is etched using a beam, such as an ion beam, electron beam, or laser beam, or using a chemical etch. After etching, the implanted areas are etched deeper into the sample, providing a pattern of troughs.

In some embodiments, charged particle beam etching is performed using a precursor gas which reacts with substrate material in the presence of the charged particle beam. The precursor reacts differently with different materials of the work piece, selectively etching some materials faster than others. In some embodiments, the beam-assisted etch rate of portions of the work piece in which ions have been implanted is reduced, leaving raised areas corresponding to the implanted regions. In other embodiments, the implanted regions etch faster than the non-implanted regions, leaving depressions in the surface corresponding to the implanted regions.

The invention has broad applicability and can provide many benefits as described and shown in the examples above. Although the description of the present invention above is mainly directed at methods of preparing ultra-thin TEM samples, various embodiments of the invention can be used on any work piece. The hardening phenomenon can be used effectively on the surface of bulk (not thinned) samples as well. Embodiments can be used to produce reinforcing structures, or raised regions for other purposes, in any structure.

Some embodiments for lamella preparation could be applied to samples that are thinned in the vacuum chamber but removed from the substrate outside the vacuum chamber (ex-situ-type samples) or to samples extracted from the substrate and thinned after mounting on a TEM grid inside the vacuum chamber (in-situ-type samples).

The embodiments will vary greatly depending upon the specific application, and not every embodiment will provide all of the benefits and meet all of the objectives that are achievable by the invention. Particle beam systems suitable for carrying out the present invention are commercially available, for example, from FEI Company, the assignee of the present application.

It should be recognized that an apparatus performing the operation of such a method would further be within the scope of the present invention.

Whenever the terms "automatic," "automated," or similar terms are used herein, those terms will be understood to include manual initiation of the automatic or automated process or step. In the following discussion and in the claims, the terms "including" and "comprising" are used in an open-ended fashion, and thus should be interpreted to mean "including, but not limited to . . . ." The term "integrated circuit" refers to a set of electronic components and their interconnections (internal electrical circuit elements, collectively) that are patterned on the surface of a microchip. The term "semiconductor device" refers generically to an integrated circuit (IC), which may be integral to a semiconductor wafer, simulated from a wafer, or packaged for use on a circuit board. The term "FIB" or "focused ion beam" is used herein to refer to any collimated ion beam, including a beam focused by ion optics and shaped ion beams.

To the extent that any term is not specially defined in this specification, the intent is that the term is to be given its plain and ordinary meaning. The accompanying drawings are intended to aid in understanding the present invention and, unless otherwise indicated, are not drawn to scale. By microscopic is meant on a scale smaller than millimeters, such as a scale of microns or a scale of nanometers.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follow:

1. A method for preparing a thin, reinforced lamellar structure using a charged particle beam system, comprising:
    forming a lamella from a sample material;
    applying to the lamella a hardening material in a pattern corresponding to a reinforcing structure by directing a focused beam of ions onto a face of the lamella to implant ions into the face according to the pattern; and
    thinning the lamella by milling, wherein a region of the lamella corresponding to the reinforcing structure is milled at a slower rate than a region of the lamella without the hardening material, leaving the reinforcing structure where the hardening material was applied to mechanically strengthen the lamella.

2. The method of claim 1 in which:
    the focused beam of ions is a first beam;
    thinning the lamella comprises milling the lamella with a second beam; and
    the second beam mills a region of the lamella implanted with ions at a rate that is at least 20% lower than a rate at which the second beam mills a region of the lamella not implanted with ions.

3. The method of claim 1 in which directing a focused ion beam toward the lamella to implant ions includes directing $Be^+$, $Ga^+$, $Xe^+$, $Ar^+$, $O^+$, $In^+$, $Si^+$, $Kr^+$, or $Bi^+$ ions.

4. The method of claim 3 in which directing a focused ion beam toward the lamella to implant ions includes directing a beam of beryllium ions towards the lamella.

5. The method of claim 1 in which directing a focused ion beam toward the lamella to implant ions into the lamella includes providing an ion dose of between 0.1-1.0 $nC/\mu m^2$.

6. The method of claim 1 in which applying a hardening material and milling the lamella are performed by a single focusing column in the charged particle beam system.

7. The method of claim 6 in which the single focusing column comprises of a liquid metal alloy source or a plasma ion source and a mass filter to select the ions.

8. The method of claim 1 in which the lamella has a final thickness of less than 20 nm.

9. The method of claim 1, wherein thinning the lamella by milling comprises:
    milling the lamella with a focused ion beam comprising ions different than the ions implanted into the lamella; or
    milling the lamella with a focused ion beam having a beam energy different than the focused beam of ions used for implanting ions into the lamella.

10. The method of claim 1 wherein applying to the lamella a hardening material by directing a focused beam of ions toward the lamella to implant ions into the lamella comprises applying a hardening material without beam-induced deposition.

11. The method of claim 1 wherein applying to the lamella a hardening material in a pattern corresponding to a reinforcing structure by directing a focused beam of ions toward the lamella to implant ions into the lamella comprises implanting ions into an implanted area and wherein thinning the lamella by milling comprises milling a milled area and wherein the milled area is larger than the implanted area.

12. The method of claim 1 wherein the reinforcing structure reduces bending of the lamella.

13. A method, comprising:

forming a lamella from a bulk sample;

directing a first focused ion beam into a face of the lamella such that ions are implanted into the face in a pattern, the ions implanted being of a species that hardens the material of the lamella where implanted; and thinning the lamella using a second focused ion beam, wherein the second focused ion beam thins a region of the lamella implanted with the ions at a slower rate than a region of the lamella not implanted with the ions, thereby exposing a raised structure that corresponds to the pattern and mechanically reinforces the lamella.

14. The method of claim 13, further comprising observing a feature in the lamella using a transmission electron microscope.

\* \* \* \* \*